United States Patent
Lipps et al.

(10) Patent No.: US 7,589,062 B2
(45) Date of Patent: Sep. 15, 2009

(54) TWO SYNTHETIC PEPTIDES FOR TREATMENT AND PREVENTION OF CANCERS

(76) Inventors: Binie V. Lipps, 4509 Mimosa Dr., Bellaire, TX (US) 77401; Frederick W. Lipps, 4509 Mimosa Dr., Bellaire, TX (US) 77401

( * ) Notice: Subject to any disclaimer, the term of this patent is extended or adjusted under 35 U.S.C. 154(b) by 142 days.

(21) Appl. No.: 11/709,960

(22) Filed: Feb. 23, 2007

(65) Prior Publication Data
US 2007/0232547 A1    Oct. 4, 2007

Related U.S. Application Data

(62) Division of application No. 10/174,692, filed on Jun. 19, 2002, now Pat. No. 7,183,258.

(51) Int. Cl.
*A61K 38/08* (2006.01)
(52) U.S. Cl. ......................................................... 514/13
(58) Field of Classification Search ..................... 514/13
See application file for complete search history.

(56) References Cited

U.S. PATENT DOCUMENTS 4,672,107 A * 6/1987 Kilmon ...................... 530/350

OTHER PUBLICATIONS

Nag et al. Cancer Research 1995; 55: 360-368.*
Talmadge et al. (The American Journal of Pathology 2007; vol. 170; 793-804.*
Freshney (Culture of Animal Cells, A Manual of Basic Technique, Alan R. Liss, Inc., 1983, New York, p. 4).*
Dermer (Bio/Technology, 1994, 12:320).*
Granziero et al. (Eur. J. Immunol. 1999, 29:1127-1138).*
Byers, T. (CA Journal, vol. 49, No. 6, Nov./Dec. 1999).*
Gura (Science, v278, 1997, pp. 1041-1042).*

* cited by examiner

*Primary Examiner*—Brandon J Fetterolf
(74) *Attorney, Agent, or Firm*—John R Casperson

(57) ABSTRACT

Two synthetic peptides, Atroporin (AT) and Kaotree (KT), each consisting of ten amino acids and their use for the treatment and/or prevention of various types of cancers is disclosed. The amino acid sequence from the N-terminal for AT is Phe-Cys-Arg-Phe-Leu-Leu-Cys-Pro-Ser-Arg, and for KT is Pro-Pro-Gly-Asn-Gln-Pro-Asp-Ala-Asp-Ser.

10 Claims, No Drawings

TWO SYNTHETIC PEPTIDES FOR TREATMENT AND PREVENTION OF CANCERS

CROSS-REFERENCE TO RELATED APPLICATION

This application is a division of application Ser. No. 10/174,692, filed Jun. 19, 2002, now U.S. Pat. No 7,183,258.

TECHNICAL FIELD

In one aspect, the invention relates to synthetic peptides. In another aspect, the invention relates to the use of synthetic peptides in the prevention of, and/or treatment of, cancers in humans.

BACKGROUND OF THE INVENTION

Currently, numerous chemicals are being used to treat various types of cancers and such treatment is termed as chemotherapy. Chemotherapy is associated with adverse side effects, such as hair loss, diarrhea, skin rash etc. simply because the chemicals used to kill cancer cells also affect normal cells adversely. Chemotherapy requires different chemical drugs to treat different types of cancers.

In our U.S. Pat. No. 5,565,431, the disclosure of which is incorporated herein by reference, cancer cell inhibitors Atroporin (AT) and Kaotree (KT) were isolated by fractionating venoms of *Crotalus atrox* and *Naja, kaouthia* snakes respectively by high pressure liquid chromatography (HPLC). Atroporin (AT) had a molecular weight of approximately 35,000 Daltons, whereas Kaotree (KT) had a molecular weight of approximately 6,000 Daltons. The homogeneous preparation of AT and KT showed killing effects on several types of human (breast, colon, liver, ovary etc.) and animal cancer cells in concentration as low as 0.5 µg/ml, and having no effect on normal mouse kidney, liver and spleen cells as high as 5.0 µg/ml. Both Atroporin and Kaotree exhibited the property of preventing the formation and regression of ascitic tumors caused by myeloma cells in Balb/c mice. The combination of AT and KT showed elevated anticancer activity in both in vitro and in vivo systems.

The relatively large molecular sizes of intact AT and KT limit the routes by which they can be administered.

The relatively large molecular sizes of AT and KT also raises the possibility of patient adverse reactions.

The fact that AT and KT are derived from venoms further makes gaining commercial acceptance more difficult.

Smaller molecules which mimic the properties of AT and KT and are not derived from venom would be very desirable.

OBJECTS OF THE INVENTION

It is an object of this invention to claim synthetic (Syn) peptides based on active fragments of AT and KT and their use to treat and prevent various types of cancer. Syn AT and Syn KT individually or in combination show cytolytic activity to a wide range of tumor cells, in both in vitro and in vivo systems. A further object of this invention is to provide a non toxic cancer treatment without a typical adverse effect caused by usual chemotherapy because AT and KT having selectively killing effects on cancer cells leaving normal cells unaffected. Furthermore, the combination of AT and KT exhibits enhanced cytolytic activity for certain types of cancer. Hence, it is a further object of the invention to claim that the combination may lead to more effective cancer therapy.

The treatment in liquid form can be given by buccal route under the tongue, or by injections. The bioavailability of such small molecules having low molecular weight will get into the circulation immediately like chemical drugs without getting degraded.

SUMMARY OF THE INVENTION

In one embodiment of the invention, we provide a synthetic AT, which we broadly characterize as a peptide comprising at least the first five amino acids from the N-terminal of the sequence Phe-Cys-Arg-Phe-Leu-Leu-Cys-Pro-Ser-Arg-Ser-Leu-Leu and no more than 25 amino acids total.

In another embodiment of the invention, we provide a synthetic KT, which we broadly characterize as peptide comprising at least the first five amino acids from the N-terminal of the sequence Pro-Pro-Gly-Asn-Gln-Pro-Asp-Ala-Asp-Ser-Asn and no more than 25 amino acids total.

In a further embodiment of the invention, we provide a cancer treatment method, which we broadly characterize as administering a cytolytically effective amount of a cytolytic agent comprising at least one of the above peptides to a cancer patient in a manner to reach the bloodstream of the patient.

In another embodiment, we provide a method for preventing symptomatic cancer in a patient susceptible to same by administering to said patient preventative amount of a cytolytic agent comprising at least one of the above peptides.

DETAILED DESCRIPTION OF THE INVENTION

Cancer cell inhibitors Atroporin (AT) and Kaotree (KT) were isolated by fractionating *Crotalus atrox* and *Naja kaouthia* snake venoms respectively by high pressure liquid chromatography. The present invention relates to the identification of the active domains/fragments of the natural AT and KT, which mimic the cytolytic activity of the parent molecules against cancer cells in vitro and in animals, and the production of synthetic peptides which mimic the cytolytic activity of the fragments.

The most active fragment for AT consisted of 13 of amino acids and had the sequence (SEQ. ID. NO.: 1)
Phe-Cys-Arg-Phe-Leu-Leu-Cys-Pro-Ser-Arg-Ser-Leu-Leu.

The most active fragment for KT consisted of 11 amino acids and had the sequence (SEQ. ID. NO.: 2)
Pro-Pro-Gly-Asn-Gln-Pro-Asp-Ala-Asp-Ser-Asn.

Two synthetic constructs, consisting often and five amino acids, were made based on portions of these fragments.

The two synthetic constructs for AT, from N-terminal, were:

SEQ. ID. NO. 3: Phe-Cys-Arg-Phe-Leu-Leu-Cys-Pro-Ser-Arg consisting of 10 amino acids, and SEQ. ID. NO. 4: Phe-Cys-Arg-Phe-Leu consisting of five amino acids.

The two synthetic constructs for KT, from the N-terminal, were:

SEQ. ID. NO. 5: Pro-Pro-Gly-Asn-Gln-Pro-Asp-Ala-Asp-Ser consisting of 10 amino acids, and.

SEQ. ID. NO. 6: Pro-Pro-Gly-Asn-Gln consisting of five amino acids.

In tests, the synthetic 10 amino acid peptides proved most active, and the invention relates primarily to these synthetic versions of AT and KT, each consisting of ten amino acids, which are inhibitory to cancer cells. Syn. AT and KT individually or in combination selectively kill various types of cancer cells when tested in cell cultures.

In mice the treatment with AT or KT prolong the incubation periods for the formation of ascitic tumors caused by SP/2 cancer cells in comparison to the controls, for death. The combination of AT and KT treatment caused 50% survival in mice in comparison to the untreated controls. Based upon these results, the combination of syn. AT and KT is preferably proposed to treat various types of cancers in humans including Kaposi sarcoma in AIDS patients.

Conversion of AT and KT to Synthetic Versions: We realized that natural products specially coming from snake venoms will have resistance from FDA. Furthermore, production will depend on the availability of venoms. By our proprietary technology and pains taking research, anti-cancer active domains for natural AT and KT were identified. Synthetic peptides consisting of ten amino acids for each were made using well known automated procedures and were designated as syn AT and syn KT.

Purification of AT and KT from Snake Venoms: The homogeneous preparations of natural AT and KT were obtained by fractionating venoms of C. atrox and N. kaouthia on HPLC using ion exchange column and gradient Trizma buffer pH 7.4 (U.S. Pat. No. 5,565,431 1996; entitled, "Cancer Cell Inhibitors and Method").

Trypsin Digestion of Natural AT and KT: Purified homogeneous preparations of AT and KT were treated with trypsin dissolved in 0.1 M ammonium bicarbonate buffer pH 8.0. The AT and KT proteins individually were mixed with trypsin in 40:1 ratio. Precisely 5 mg of AT or KT was mixed with 0.125 mg of trypsin. The mixtures were incubated at 37° C. to cause fragmentation at arginine and lysine sites. After 18 hours of incubation the reaction was stopped by cooling the mixtures at 4° C.

Separation of Trypsin Digested Fragments: The fragments of AT and KT digested with trypsin were separated on HPLC. The fragments for AT and KT were collected individually and dialyzed against water using 500-Dalton molecular weight cutoff tubing (Spectrum Co. USA). The protein concentration of each fragment was measured by spectrophotometer using a protein kit from Bio-Rad Co. (USA). Each fragment was adjusted in concentration to 100 µg/ml with 0.05 M phosphate buffered saline (PBS). The fragments of trypsin digested AT and KT were separated on HPLC. HPLC separation resolved AT resolves into 7 fragments and KT 13 fragments.

Biological Activity of Fragments on SP/2 cells: The cytolytic activity of the trypsin digested fragments of AT and KT were tested on $10^5$ SP/2 cells. Dulbecco Modified Eagle's Medium (DMEM) containing 10% newborn calf serum (NBCS), L-glutamine and antibiotics penicillin and streptomycin was used to grow SP/2 cells. Initially, each fraction was tested on cells grown in 48 well plate at 37° C. in a humid CO2 incubator. The serum free medium containing different concentrations such as 20, 10, 5, 2.5 and 1.0 µg/ml of each fragment was tested. Control cells received PBS to serve as controls.

Identification of Active Fragment:

The tests were read after three days. It was revealed that one of the fragments for each AT and KT showed the highest cytolytic activity on SP/2 cells. Those fragments were considered as the active domains for cancer cell inhibitor. The fragment 6 for AT and 10 for KT were found to be the most active for cytolytic activity when tested on SP/2 cells. The fragment 6 for AT and the fragment 10 for KT were considered as the active domains for cytolytic activity. The most active fragments 6 for AT and 10 for KT were sequenced for their amino acids composition. The sequence for the most active fragment from N-terminal for AT consisting of 13 amino acids was found to be Phe-Cys-Arg-Phe-Leu-Leu-Cys-Pro-Ser-Arg-Ser-Leu-Leu. The sequence for the most active fragment from N-terminal for KT consisting of 11 amino acids was found to be Pro-Pro-Gly-Asn-Gln-Pro-Asp-Ala-Asp-Ser-Asn.

Conversion of Active Domain to Synthetic Peptides:

Two synthetic constructs, consisting of ten and five amino acids for each, were made from the most active fragment of AT and KT.

The two synthetic constructs for AT from N-terminal of SEQ ID. NO. 1 were:

SEQ. ID. NO. 3, Phe-Cys-Arg-Phe-Leu-Leu-Cys-Pro-Ser-Arg consisting of 10 amino acids, and SEQ. ID. NO. 4, Phe-Cys-Arg-Phe-Leu consisting of five amino acids.

The two synthetic constructs for KT from N-terminal of SEQ ID. NO. 2 were:

SEQ. ID. NO. 5, Pro-Pro-Gly-Asn-Gln-Pro-Asp-Ala-Asp-Ser consisting of 10 amino acids, and SEQ. ID. NO. 6, Pro-Pro-Gly-Asn-Gln consisting of five amino acids.

In vitro Biological Activity of Syn AT and Syn KT:

Biological cytolytic activity of AT and KT at various concentrations ranging from 3.5, 6.25, 12.5 and 25 µg/ml were tested on human cancer cells and SP/2 mouse myeloma cells.

The results were read microscopically the results are shown in Table 1. The combination AT+KT was 50% by weight of each.

TABLE 1

Cytolytic effect of syn AT and syn KT individually and in combination on cancer cells.

| Agent | µg/ml | % Cytolyic cells | | | | | |
|---|---|---|---|---|---|---|---|
| | | HBL-100 | BT-20 | HT-29 | Sk-ov-3 | CCL-13 | SP/2 |
| Atroporin | 25 | 100 | 100 | 100 | 100 | 100 | 100 |
| | 12.5 | 50 | 50 | 100 | 100 | 100 | 50 |
| | 6.25 | 0 | 0 | 0 | 100 | 50 | 0 |
| | 3.12 | 0 | 0 | 0 | 0 | 0 | 0 |
| Kaotree | 25 | 100 | 100 | 100 | 100 | 100 | 100 |
| | 12.5 | 100 | 75 | 100 | 100 | 100 | 100 |
| | 6.25 | 50 | 0 | 0 | 50 | 0 | 50 |
| | 3.12 | 0 | 0 | 0 | 0 | 0 | 0 |
| Atroporin + | 25 | 100 | 100 | 100 | 100 | 100 | 100 |
| Kaotree | 12.5 | 100 | 100 | 100 | 100 | 100 | 100 |
| | 6.25 | 100 | 0 | 50 | 100 | 50 | 50 |
| | 3.12 | 0 | 0 | 0 | 0 | 0 | 0 |

HBL-100 - cancer of breast
BT-20 - cancer of breast
HT-29 - cancer of colon
Sk-ov-3 - cancer of ovary
CCL-13 - cancer of mouth
SP/2 - mouse myeloma Results of table 1 show the killing effect of syn. AT and syn KT individually on cancer cells at varying concentrations. The results show that syn. KT is more cytolytic than AT in similar concentration for HBL-100, BT-20, breast cancer cells. AT is more cytolytic to Sk-ov-3 ovarian cancer cells than AT in similar concentration. However, combination of AT and KT is more cytolytic than the individual.

Anti Cancer Activity of Synthetic AT and KT In Vivo: Adult Balb/c mice were injected intra-peritoneally with 0.5 ml containing 2 million SP/2 cancer cells. Mice were divided into four groups. Starting from day one of post injection the mice were treated with AT and KT individually and the combination of both at 200 µg/ml concentration. Doses of 0.5 ml containing 100 µg/mouse were given for seven consecutive days and the control mice received 0.5 ml PBS. Results are shown in table 2.

TABLE 2

Treatment versus Incubation period for survival in days

| Group | Treatment | Survival |
|---|---|---|
| I | PBS | 23 days |
| II | Syn AT | 30 days |
| III | SYN KT | 37 days |
| IV | Both AT & KT | 50% at 60 days |

Results show that the treatment with syn. AT and KT individually prolonged the incubation period for the development of ascitic tumors to cause death, 30 and 37 days versus 23 days for untreated or injected with PBS. Combination of syn-AT and KT yielded 50% survival. It is noteworthy that the treatment period continued for only 7 days.

In vitro combination of AT and KT provides enhanced killing effect on various types of cancer cells. In vivo combination of AT and KT prolongs incubation period to form tumors and showed 50% survival, therefore the combination of syn AT and KT is preferably proposed for human therapy. For such use, the composition will generally contain, based on weight, in the range of 10% to 90% of AT, balance KT, usually in the range of 30% to 70% AT, balance KT.

Based on a 50 kilogram human having approximately 2500 times the mass of a 20 gram mouse, an equivalent dose of peptide(s) (alone or combined) for humans as was tested on mice is believed on the order of 250 milligrams/day. For treating cancer in humans, a dosage level in the range of about 5 milligrams to 5,000 milligrams daily is believed broadly suitable, depending on the size of the patient, the severity and type of cancer, and the period of treatment. It is expected that the dosage will generally be in the range of 100 to 1,000 milligrams per day and continue for a period of time in the range of 1 to 100 days, generally in the range of 5 to 50 days. Because the peptides are of low molecular weight, they can be orally or bucally administered if desired, although intravenous administration will also be suitable.

Prevention of Cancer: We propose the combination of synthetic versions of cancer cell inhibitors AT and KT as an effective, and, most importantly, non-toxic treatment for prevention of cancer.

In the prosperous countries, roughly 20%, or one in five will die of cancer. The most frequently occurring cancers worldwide in descending order are: stomach, lung, breast, colon/rectum, cervix and mouth/pharynx. Surgery, chemotherapy and radiation show limited success, but these procedures remove or destroy normal cells along with cancer cells. The search for treatments for cancer has been vigorously pursued for over a half century, and the use of chemicals to treat cancer continues. The treatment of cancer needs to be changed from chemotherapy to biotherapy using small biological peptides having minimal, or no adverse effects.

To date, there is no preventive therapy for cancer. We strongly believe that the syn AT and KT, being capable of killing selectively cancer cells, should fill this gap. Population of people having predisposition for cancer, due to hereditary or other reasons should be given this treatment, may be once or twice a year. AT and KT will function like vaccine for prevention of cancer, although their activity is not due to the antibodies production but due to selective killing effect. Of course, the necessary controlled studies will require long period of time and a lot of investment.

For this application, it is expected that a dosage level in the range of 5 milligrams to 250 milligrams per day continuing for a period of time in the range of 1 to 10 days will be suitable, to be repeated every few months.

Treatment or Prevention of Recurrence for Cancer: During a normal healthy life cancer cells are constantly formed due to mutation and are removed at the same rate by the natural killer cells. If, for whatever reason, the cancer cell number overrides the natural killer cell population, the cancer cells become established in body organs. A tumor is an aggregation of cancer cells due to excessive rapid growth property of cancer cells. By the time the patient is diagnosed for cancer, the cancer may be metastasized. Diagnosis generally leads to surgery to remove cancer growth or tumor, followed by chemotherapy. Even after surgery most of the times the cancer comes back.

Syn. peptides AT and KT are non toxic to normal cells their killing effect is selectively for various types of cancer cells. Combination of syn. AT and KT treatment can cause regression of tumors, depending upon the size of the cancer tumor. In such case where surgery is inevitable the combination of AT and KT can serve as a treatment to prevent recurrence of cancer.

Further Details

The syn AT peptide contains at least the first five amino acids from the N-terminal of the sequence Phe-Cys-Arg-Phe-Leu-Leu-Cys-Pro-Ser-Arg-Ser-Leu-Leu somewhere in its backbone and no more than 25 amino acids total. Preferably, the syn AT peptide contains no more than 20 amino acids, and more preferably no more than 15 amino acids, because smaller peptides are less expensive to synthesize. On the other hand, the syn AT which showed the greatest promise had 10 amino acids, so it is most preferred that the syn AT peptide consists of at least the first 10 amino acids of the stated sequence.

The syn KT peptide contains at least the first five amino acids from the N-terminal of the sequence Pro-Pro-Gly-Asn-Gln-Pro-Asp-Ala-Asp-Ser-Asn somewhere in its backbone and no more than 25 amino acids total. Preferably, the syn KT peptide contains no more than than 20 amino acids, and more preferably no more than 15 amino acids, because smaller peptides are less expensive to synthesize. On the other hand, the syn KT which showed the greatest promise had 10 amino acids, so the most preferred syn KT consists of at least the first 10 amino acids of the sequence.

The syn AT and syn KT peptides, alone or together, constitute cytolytic agents and thus may be used to treat a human cancer patient by administering an effective amount thereof to the patient in a manner to reach the bloodstream. Because the peptides are small, a variety of administration techniques can be used, including nasal insufflation, buccal administration, oral ingestion, intravenous injection and intramuscular injection. It is expected generally that in the range of 5 milligrams to 5,000 milligrams of the cytolytic agent will be administered daily over a period of time in the range of 1 to 100 days, and that the cancers will generally be from the group stomach cancer, lung cancer, breast cancer, colon/rectum cancer, cervical cancer, mouth/pharynx cancer, and Kaposi sarcoma. Utilizing both of the peptides together would be preferred. For the prevention of these cancers in susceptible populations, it is expected in the range of 5 milligrams to 250 milligrams would be administered daily for a period of time in the range of 1 to 10 days.

While certain preferred embodiments of the invention have been described herein, the invention is not to be construed as being so limited, except to the extent that such limitations are found in the claims.

What is claimed is:

1. A method for treating a human cancer patient comprising administering an effective amount of a cytolytic agent to said patient in a manner to reach the bloodstream of the patient, said cytolytic agent comprising a peptide selected from the group consisting of SEQ. ID. NO: 1 and a fragment of SEQ ID NO: 1 which contains at least the first five amino acids thereof.

2. A method as in claim 1 wherein the patient is a victim of a cancer selected from the group consisting of stomach cancer, lung cancer, breast cancer, colon/rectum cancer, cervical cancer, mouth/pharynx cancer, and Kaposi sarcoma,
the administration technique is selected from the group consisting of nasal insufflation, buccal administration, oral ingestion, intravenous injection and intramuscular injection, and the cytolytic agent consists of SEQ. ID. NO: 3.

3. A method as in claim 1 wherein
5 milligrams to 5,000 milligrams of the cytolytic agent are administered daily over a period of time in the range of 1 to 100 days.

4. A method for treating a human cancer patient comprising administering an effective amount of a cytolytic agent to said patient in a manner to reach the bloodstream of the patient, said cytolytic agent comprising a peptide selected from the group consisting of SEQ. ID. NO: 2 and a fragment of SEQ. ID. NO: 2 which contains at least the first five amino acids thereof.

5. A method as in claim 4 wherein the patient is a victim of a cancer selected from the group consisting of stomach cancer, lung cancer, breast cancer, colon/rectum cancer, cervical cancer, mouth/pharynx cancer, and Kaposi sarcoma,
the administration technique is selected from the group consisting of nasal insufflation, buccal administration, oral ingestion, intravenous injection and intramuscular injection, and the cytolytic agent consists of SEQ. ID. NO: 5.

6. A method as in claim 4 wherein
5 milligrams to 5,000 milligrams of the cytolytic agent are administered daily over a period of time in the range of 1 to 100 days.

7. A method for treating a human cancer patient comprising administering an effective amount of a cytolytic agent to said patient in a manner to reach the bloodstream of the patient,
said cytolytic agent comprising
a first peptide selected from the group consisting of SEQ. ID. NO: 1 and a fragment of SEQ ID NO: 1 which contains at least the first five amino acids thereof, and
a second peptide selected from the group consisting of SEQ. ID. NO: 2 and a fragment of SEQ. ID. NO: 2 which contains at least the first five amino acids thereof.

8. A method as in claim 7 wherein the cytolytic agent comprises
a 10 amino acid first peptide consisting of SEQ. ID. NO: 3, and
a 10 amino acid second peptide consisting of SEQ. ID. NO: 5.

9. A method as in claim 7 wherein the patient is a victim of a cancer selected from the group consisting of stomach cancer, lung cancer, breast cancer, colon/rectum cancer, cervical cancer, mouth/pharynx cancer, and Kaposi sarcoma, and the administration technique is selected from the group consisting of nasal insufflation, buccal administration, oral ingestion, intravenous injection and intramuscular injection.

10. A method as in claim 7 wherein
5 milligrams to 5,000 milligrams of the cytolytic agent are administered daily over a period of time in the range of 1 to 100 days.

* * * * *

```
                       SEQUENCE LISTING

<160> NUMBER OF SEQ ID NOS: 6

<210> SEQ ID NO 1
   <211> LENGTH: 13
   <212> TYPE: PRT
   <213> ORGANISM: Artificial
   <220> FEATURE:
   <223> OTHER INFORMATION: Fragment of 35,000 Dalton Protein isolated from
         Crotalus atrox venom (see US 5,,6431)

<400> SEQUENCE: 1

Phe Cys Arg Phe Leu Leu Cys Pro Ser Arg Ser Leu Leu
   1               5                   10

<210> SEQ ID NO 2
   <211> LENGTH: 11
   <212> TYPE: PRT
   <213> ORGANISM: Artificial
   <220> FEATURE:
   <223> OTHER INFORMATION: Fragment from 6,000 Dalton Protein Isolated
         from Naja Kaouthia Venom (see US 5,665,431)

<400> SEQUENCE: 2

Pro Pro Gly Asn Gln Pro Asp Ala Asp Ser Asn
   1               5                   10

<210> SEQ ID NO 3
   <211> LENGTH: 10
   <212> TYPE: PRT
   <213> ORGANISM: Artificial
   <220> FEATURE:
   <223> OTHER INFORMATION: Synthetic.  Fragment of SEQ ID NO: 1.

<400> SEQUENCE: 3

Phe Cys Arg Phe Leu Leu Cys Pro Ser Arg
   1               5                   10

<210> SEQ ID NO 4
   <211> LENGTH: 5
   <212> TYPE: PRT
   <213> ORGANISM: Artificial
```

```
<220> FEATURE:
<223> OTHER INFORMATION: Synthetic.  Fragment of SEQ ID NO: 3.

<400> SEQUENCE: 4

Phe Cys Arg Phe Leu
1               5

<210> SEQ ID NO 5
<211> LENGTH: 11
<212> TYPE: PRT
<213> ORGANISM: Artificial
<220> FEATURE:
<223> OTHER INFORMATION: Synthetic.  Fragment of SEQ ID NO: 2

<400> SEQUENCE: 5

Pro Pro Gly Asn Gln Pro Asp Ala Asp Ser Asn
1               5                   10

<210> SEQ ID NO 6
<211> LENGTH: 5
<212> TYPE: PRT
<213> ORGANISM: Artificial
<220> FEATURE:
<223> OTHER INFORMATION: Synthetic.  Fragment of SEQ ID NO: 5.

<400> SEQUENCE: 6

Pro Pro Gly Asn Gln
1               5
```